United States Patent [19]

Drent

[11] 4,426,331
[45] Jan. 17, 1984

[54] PREPARATION OF CARBONATE ESTERS IN THE PRESENCE OF SULFONES

[75] Inventor: Eit Drent, Amsterdam, Netherlands

[73] Assignee: Shell Oil Company, Houston, Tex.

[21] Appl. No.: 399,167

[22] Filed: Jul. 19, 1982

[30] Foreign Application Priority Data

Jul. 30, 1981 [GB] United Kingdom ............... 8123325

[51] Int. Cl.$^3$ .............................................. C07C 68/00
[52] U.S. Cl. ..................................... 260/463; 549/28; 549/87; 568/28
[58] Field of Search .................... 260/463; 549/87, 28; 568/28

[56] References Cited

U.S. PATENT DOCUMENTS

Re. 29,338  8/1977  Perrotti et al. ............... 260/463
4,218,391  8/1980  Romano et al. ............... 260/463
4,318,862  5/1982  Romano et al. ............... 260/463

FOREIGN PATENT DOCUMENTS 3016187  10/1981  Fed. Rep. of Germany .
1303756  1/1973  United Kingdom .

OTHER PUBLICATIONS

Romano et al., Ind. Eng. Chem. Prod. Res. Dev., vol. 19, 396-403 (1980).
Othmer, K. Encyclopedia of Chemical Technology, vol. 19, pp. 250-254, IInd. Edt. (1969), Interscience, Pub. N.Y.

Primary Examiner—Donald G. Daus
Assistant Examiner—Chabi C. Kalita

[57] ABSTRACT

A process for the oxidative carbonylation of an alcohol to produce a carbonate, which comprises reacting together carbon monoxide, oxygen and an alcohol, in the presence of a copper compound and in the presence of a sulfone.

10 Claims, No Drawings

PREPARATION OF CARBONATE ESTERS IN THE PRESENCE OF SULFONES

BACKGROUND OF THE INVENTION

This invention relates to improvement in the process for the preparation of carbonate esters by oxidative carbonylation of alcohols.

Processes for the carbonylation of alcohols have recognized utility in organic synthesis. For instance, the organic carbonate products of such processes have particular value as reactants in the preparation of isocyanates and polycarbonates, and as alkylating agents.

It is known that oxidative carbonylation of an alcohol (ROH) can be carried out by reaction with carbon monoxide and oxygen, according to the equation:

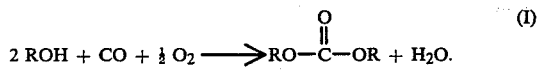

Great Britain Patent Specification No. 1,303,756 discloses such a process for which R is a hydrocarbyl group (particularly alkyl, aryl or cycloalkyl) and the reaction is catalyzed by a complexed compound of a metal in Group IB, IIB, or VIII of the Periodic Table, for example, a complex derived from a copper salt, e.g., $Cu_2Cl_2$, and an organic base, e.g., pyridine.

However, Belgian Patent Specification No. 859,272 and also a recent publication (Ind. Eng. Chem. Prod. Res. Dev., 1980, pp. 396–403) point out that such a process has a number of disadvantages. Preference is indicated for use of a simple metal salt, most preferably a copper (I) salt, without a complexing agent. The use of copper (II) salts is said to lead to large quantities of by-products, particularly halogen derivatives when copper (II) halides are used as catalysts.

In either case, these prior art processes are found to be substantially and adversely influenced by the presence of water in the reaction medium. (The detrimental effect of water is addressed in detail on pages 400 and 401 of the publication cited above.) Disadvantages resulting from the presence of water are observed both in the reaction rate and in the selectivity to the desired carbonate. Since water is produced during the carbonylation reaction (equation I) it has been necessary to terminate reactions according to processes of the prior art at low levels of conversion in order to maintain high rates and selectivities.

SUMMARY OF THE INVENTION

It has now been found that in a process for the oxidative carbonylation of an alcohol to produce an organic carbonate, which comprises the reaction of the alcohol with carbon monoxide and oxygen in the presence of a copper compound, improvement is provided by carrying out the reaction in the further presence of a sulfone compound. Specifically, the presence of the sulfone provides both increased rate of reaction and enhanced selectivity to the desired organic carbonate at a given level of conversion of the alcohol starting material.

DESCRIPTION OF THE PREFERRED EMBODIMENTS

Apart from aspects relating to the presence of a sulfone in the reaction mixture, the alcohol carbonylation process of the invention can generally be accomplished applying reactants and processing procedures and conditions known to be suitable or preferred in the art for this purpose.

Thus, the alcohol reactant may suitably comprise any one or more different compounds, each containing one or more hydroxyl groups. The use as reactants of alcohols having multiple hydroxyl groups typically results in polymeric products. The (or each) hydroxyl group is preferably attached to an aliphatic carbon atom of the alcohol molecule. Thus, for example, the alcohol may be an alkanol or an alkenol or, alternatively, an alkanol or alkenol in which the alkyl or alkenyl group is optionally substituted with one or more inert substituents, e.g., halogen atoms and phenyl, alkoxy, alkoxycarbonyl, and alkyl carbonyl groups. Most preferably, in addition to the hydroxyl group or groups the alcohol is substituted (if at all) only by hydrocarbyl moieties as, for instance, is the case in methanol, ethanol benzyl alcohol, allyl alcohol, and the various isomeric propanols and butanols. Preference can also be stated for alkanol reactants having no more than about 20 carbon atoms, while those having less than about 10 carbon atoms are more preferred.

As generally disclosed in the prior art, the carbonylation reaction is suitably catalyzed by a copper compound in either the I or II valent state. A copper II compound is generally preferred for this reason. This compound may be a simple salt, for example, a salt with an organic acid such as acetic acid or with a mineral acid such as a hydrogen halide or hydrogen cyanide. Alternatively, the compound may be a complex containing both anions and neutral ligands of the type described in the above-referenced Great Britain Specification 1,303,756. Such complexes may be preformed before introduction into the reaction mixture, or they may be generated in situ by reaction between a copper salt and a suitable donor ligand. Unexpectedly active catalysts are obtained when a copper salt (especially a copper (I) or, more preferably, a copper (II), halide compound) is added to the reaction mixture and there is further present in the mixture a tertiary aliphatic amine, very preferably a trialkylamine, for example, triethylamine. Preferably, the tertiary aliphatic amine is added in a quantity of about 0.01 to 1.0, more preferably about 0.05 to 0.9 moles per gram atom of copper.

The quantity of copper compound present in the reaction mixture is not critical, so long as it is sufficient to exert a catalytic effect. Quantities in the range of from 0.001 to 10%, especially 0.01 to 5%, calculated as gram atoms of copper per mole of alcohol reactant, are generally suitable.

In distinction to prior art carbonylation processes, the invention is conducted in the presence of a sulfone, suitably a cyclic or acyclic sulfone of the general formula

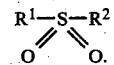

In an acyclic sulfone, each of $R^1$ and $R^2$ independently represents an optionally substituted alkyl group; in the case of a cyclic sulfone $R^1$ and $R^2$ together represent an optionally substituted alkylene group. Optional substituents may be any moieties essentially inert under the carbonylation reaction conditions, for example, halogen atoms, alkoxy groups, phenyl groups and phenoxy groups. An alkyl group $R^1$ or $R^2$ preferably has no more than about 12, more preferably no more than about 6, carbon atoms. An alkylene group represented by $R^1$ and $R^2$ together preferably has 4, 5 or 6 carbon atoms in the chain, and up to 6 carbon atoms in any alkyl side-chain. Preferably $R^1$ and $R^2$ individually represent unsubstituted alkyl groups, or $R^1$ and $R^2$ together represent an unsubstituted alkylene group.

Specific examples of suitable acyclic sulfones are dimethyl, diethyl, dipropyl, dibutyl, methyl ethyl, and methyl butyl sulfone. Specific examples of cyclic sulfones are sulfolane, 2-methylsulfolane, 3-methylsulfolane, 3-butylsulfolane, 3-isopropylsulfolane, and 2-methyl-4-butylsulfolane. The use of sulfolane is particularly preferred.

The function of the specific sulfones has been found to be critical in the context of the invention—the presence in the same system of such substances as dimethyl sulfoxide and N-methyl pyrrolidone, which might be expected to give similar results, does not produce the same advantages as a sulfone in terms of process rate and selectivity.

The quantity of sulfone used may suitably vary over a wide range. Preferably, the molar ratio of sulfone to alcohol reactant is in the range of from 0.05:1 to 20:1, while the range of from 0.25:1 to 10:1 is more preferred. If the sulfone is a liquid at the reaction temperature, it may conveniently be used in relatively large, or solvent, amounts for the liquid reaction phase, containing alcohol, catalyst, products, and, if desired, additive as indicated below. It is often most preferable to use approximately the minimum quantity of liquid sulfone required to produce a homogeneous liquid phase in the reaction mixture.

Carbon monoxide and oxygen are necessary reactants. The ratio of one to the other is not critical to the reaction process. However, safety is a principal consideration and it is advisable to operate outside recognized explosive limits. For this reason it is often desirable to conduct the reaction under a relatively high partial pressure of carbon monoxide and to meter in oxygen throughout the course of the reaction. Preferably, the gas phase of the reaction mixture is maintained at a concentration of oxygen between about 3 percent by volume (% v) and 8% v. Inert gases (for example, nitrogen) may be present in the reaction system. Air can be utilized for direct addition to the reaction mixture as the source of oxygen reactant.

Preference may be stated for carrying out the process according to the invention at a temperature in the range of from about 50° to 150° C., particularly from about 70° to 125° C. Pressures in the range of from about 10 to 100 bar, especially 30 to 80 bar, are preferred. Higher pressures are suitable, but are in general uneconomical.

In addition to alcohol, oxygen, and carbon monoxide reactants, catalyst, and sulfone, the reaction system may suitably (but optionally) contain other components. For instance, the process is preferably carried out in the presence of halide ion. The halide ion may originate from the copper salt, for example, if a copper halide is used, or it may come from another source of halide, for example, an alkali metal halide, an alkaline earth metal halide or a hydrogen halide which is added to the reaction mixture. The reaction is also preferably carried out in the presence of a base. Organic bases, such as aliphatic tertiary amines as discussed above, or alkali or alkaline earth metal carboxylates are suitable. Suitable inorganic bases include alkali and alkaline earth metal carbonates. Preferably the number of moles of base added per gram atom of copper is in the range of from 0.01 to 1, especially 0.05 to 0.9. If desired, an inert solvent may also be present in the reaction mixture, for example, a hydrocarbon or halogenated hydrocarbon such as pentane, toluene or carbon tetrachloride; an ester such as ethyl acetate; a ketone such as acetone; or an ether such as diethyl ether or tetrahydrofuran. In order to facilitate work-up of the reaction mixture, which contains water generated as a co-product along with the carbonate, it is often desirable to use an inert solvent which forms an azeotrope either with the water or with the carbonate. In this way the water and the carbonate can be separated readily.

It is considered to be of substantial advantage that the presence of water in the reaction mixture can be tolerated in the process according to the invention. Some water may even be present at the beginning of the reaction, and the presence of the amounts of water normally found in commercial forms of components of the reaction mixture presents no problem. It has been considered advisable, if not necessary, to dry such components before their use in carbonylation reactions under conventional practice.

EXAMPLES 1 TO 9

Experiments in accordance with the invention were carried out under the following general procedures. A 300 ml stirred autoclave was charged with quantities of alcohol (methanol), sulfolane, catalyst, and additional components as indicated. The sulfolane was a normal water-containing commercial grade. The autoclave was then pressurized with 50 bar carbon monoxide (except Example 1, 30 bars) and the temperature was raised to the desired level. Periodic addition was made of air (4 bar). The internal oxygen concentration was monitored to ensure that it remained at less than 8% v of the gas cap, and greater than 3% v. Pressure within the autoclave remained roughly constant, the CO removed during the course of the reaction being replaced by the nitrogen present in the air introduced. After the desired reaction time, the contents of the autoclave were removed and analyzed by gas-liquid chromatography.

The results of the experiments are presented in the following Table. In all cases, the methanol was converted to dimethylcarbonate, with virtually no by-product formation. Traces (less than 0.5%) of dimethoxymethane, methyl chloride and methyl chloroformate were the only by-products observed. In Examples 2, 4 and 6, almost no carbon monoxide remained in the autoclave after the reaction time was over. Example 5 shows that the presence of quite large quantities of water at the beginning of the reaction leads to some reduction in the rate of the reaction but no reduction in selectivity to the desired product.

TABLE OF RESULTS

| EXAMPLE NO. | CATALYST (mmol) | METH-ANOL (ml) | SULFO-LANE (ml) | OTHER COMPONENTS PRESENT | REACTION TEMPERATURE (°C.) | TIME TIME (HOURS) | CONVERSION OF METHANOL TO PRODUCTS (% MOLAR) |
|---|---|---|---|---|---|---|---|
| 1 | $CuCl_2.2H_2O$ (6) | 25 | 25 | $N(C_2H_5)_3$ (7mmol) | 90 | 1 | 10 |
| 2 | $CuCl_2.2H_2O$ (12) | 25 | 25 | $N(C_2H_5)_3$ (4mmol) | 120 | 1.5 | 31 |
| 3 | $CuCl_2.2H_2O$ (12) | 10 | 40 | none | 125 | 4 | 20 |
| 4 | $CuCl_2.2H_2O$ (12) | 10 | 40 | $N(C_2H_5)_3$ (4mmol) | 125 | 3 | 48 |
| 5 | $CuCl_2.2H_2O$ (12) | 10 | 40 | $N(C_2H_5)_3$ (4mmol) $H_2O$ (5mls) | 92 | 2 | 17 |
| 6 | $CuCl_2.2H_2O$ (12) | 5 | 45 | $N(C_2H_5)_3$ (4mmol) | 120 | 4 | 62 |
| 7 | CuCl (12) | 10 | 40 | none | 90 | 3 | 9 |
| 8 | CuCl (12) | 10 | 40 | $N(C_2H_5)_3$ (4mmol) | 90 | 3 | 15 |
| 9 | $Cu(CH_3CO_2)_2$ (12) | 25 | 25 | $N(C_2H_5)_3$ (4mmol) HCl (2ml of 37% aqueous solution) | 100 | 3 | 20 |

COMPARATIVE EXAMPLE

Example 1 was repeated exactly except that the 25 ml of sulfolane was replaced by an additional 25 ml of methanol, and the reaction time was 2. 5 hours. Under these conditions (not in accordance with the invention), less than 1% of the methanol reactant was converted to dimethylcarbonate.

I claim as my invention:

1. In a process for the preparation of carbonate esters which comprises reacting an alcohol with carbon monoxide and oxygen in the presence of a copper (II) compound as catalyst, the improvement which comprises carrying out the reaction in the further presence of a sulfone, with the provision that the molar ratio of said sulfone to said alcohol is in the range of from 0.25:1 to 10:1.

2. The process of claim 1, in which the sulfone has the formula:

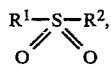

wherein each of $R^1$ and $R^2$ independently represents an optionally substituted alkyl group, or $R^1$ and $R^2$ together represent an optionally substituted alkylene group.

3. The process of claim 2, wherein $R^1$ and $R^2$ represent unsubstituted alkyl groups or $R^1$ and $R^2$ together represent an unsubstituted alkylene group.

4. The process of claim 1, in which the sulfone is sulfolane.

5. The process of claim 1, in which the copper compound contains copper in the (II) valent state.

6. The process of claim 5, in which the sulfone has the formula:

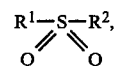

wherein each of $R^1$ and $R^2$ independently represents an optionally substituted alkyl group, or $R^1$ and $R^2$ together represent an optionally substituted alkylene group.

7. The process of claim 6, in which $R^1$ and $R^2$ represent unsubstituted alkyl groups, or $R^1$ and $R^2$ together represent an unsubstituted alkylene group.

8. The process of claim 7, in which the sulfone is sulfolane.

9. The process of claim 1, 2, 5, or 6, wherein the reaction is carried out in the presence of halide ions and of a base.

10. The process of claim 9, wherein the base is a tertiary aliphatic amine present in an amount between about 0.05 to 0.9 moles of base per gram atom of the copper compound.

* * * * *